United States Patent [19]

Zinke

[11] Patent Number: 4,901,017
[45] Date of Patent: Feb. 13, 1990

[54] GAP-MODIFIED MAGNETIC BRIDGE DEVICE FOR FRINGING FLUX ANALYSIS

[76] Inventor: Otto H. Zinke, 817 N. Jackson Dr., Fayetteville, Ark. 72701

[21] Appl. No.: 90,778

[22] Filed: Aug. 28, 1987

[51] Int. Cl.⁴ .................. G01N 27/72; G01N 27/83; G01R 33/12; G01P 15/08
[52] U.S. Cl. .................. 324/239; 73/517 R; 324/220; 324/229; 324/240; 324/207.19
[58] Field of Search ............... 324/207, 208, 222, 223, 324/228–243, 219–221; 73/517 R, 517 AV; 360/120

[56] References Cited

U.S. PATENT DOCUMENTS

| | | | |
|---|---|---|---|
| 2,660,622 | 11/1953 | Field et al. | 360/120 X |
| 2,852,618 | 9/1958 | Hansen | 360/120 |
| 3,059,749 | 10/1962 | Zinke | 324/234 X |
| 3,171,903 | 3/1965 | Wheeler et al. | 360/125 X |
| 3,379,969 | 4/1968 | Zinke | 324/239 |
| 3,534,253 | 10/1970 | Zinke | 324/239 |
| 3,626,344 | 12/1971 | Shaternikov et al. | 324/230 X |
| 3,688,056 | 8/1972 | Wiseley et al. | 360/120 X |
| 3,867,844 | 2/1975 | Shimizu et al. | 73/517 R |
| 4,079,804 | 3/1978 | Paillard | 73/517 R X |
| 4,311,051 | 1/1982 | Eon et al. | 73/517 R |
| 4,314,202 | 2/1982 | Okubo | 324/207 |
| 4,806,863 | 2/1989 | White | 324/238 X |

Primary Examiner—Gerard R. Strecker
Attorney, Agent, or Firm—Kalish & Gilster

[57] ABSTRACT

Various devices are constructed with gap-modified magnetic bridge circuits. In a magnetic bridge device for evaluation of samples, a magnetic bridge circuit has at least four arms, a driving leg and a sensing leg, one of the arms being utilized for evaluating a sample, pole pieces of a sample-evaluating arm having end faces defining between them a sample-evaluating gap. An electrically conductive gap insert produces an enhanced fringing flux exteriorly of it. The sample is placed in juxtaposition to the sample-evaluating gap for affecting the fringing flux. A driving circuit for the driving leg provides a time-varying flux path within the four arms of the bridge. A sensing device associated with the sensing leg senses changes in the sensing leg caused by changes in the fringing flux resulting from characteristics or movement of the sample. A specific single-side modification provides an accelerometer.

17 Claims, 6 Drawing Sheets

GAP-MODIFIED MAGNETIC BRIDGE DEVICE FOR FRINGING FLUX ANALYSIS

BACKGROUND AND SUMMARY OF THE INVENTION

This invention relates to magnetic bridges and more particularly to improved magnetic bridge devices providing electromagnetic evaluation of various samples and materials by measurement of the complex magnitude and phase components of an induced magnetic flux.

Magnetic bridges driven by time-varying magnetic fields (U.S. Pat. No. 3,379,969 of O. H. Zinke) can be controlled through combinations of resistances and reactances coupled to the bridge arms (U.S. Pat. No. 3,534,253 of O. H. Zinke) and used to measure conducting and/or magnetic characteristics of samples either inserted directly in the gaps in the bridge arms or inserted in the fringing fields of the gaps. For maximum sensitivity, samples have to be placed directly in the gaps in order to intersect the maximum amount of time-varying flux. If, for reasons of convenience, samples are placed in the fringing flux, the sensitivity of the bridge to the characteristics of the sample changes in the approximate ratio of the fringing flux intersected by the sample to the total flux in the gap. Thus, in the magnetic bridges described in the above two patents, the most efficient use occurs when the sample is placed directly in the gap in a bridge arm. Under these circumstances, the size of the sample which can be inspected is restricted by the width of the gap which can be used and the length of the bridge arm. For example, if an aircraft wing were to be inspected for fatigue in the aluminum skin, the bridge arms would have to be about half the width of the aircraft wing, and the gap in the bridge would have to be larger than the thickness of the wing. Such a wide gap would greatly reduce the time-varying magnetic flux because of the tendency of flux to spread as it leaves a magnetic pole (the face of the gaps). Further, and possibly more important, the eddy currents induced in the sample under such circumstances may not have paths which are appropriate to the detection of the characteristic sought. In the above example, the eddy-current paths could be of the order of the sample, the wing, while the characteristic being searched for would be small cracks appearing near the rivets in the wing. The sensitivity of the bridge would be further reduced by the ratio of the volume of the crack to the volume of the whole wing.

A solution to the problem above described, as herein set forth, involves modification of the magnetic bridge devices of the above patents. This modification, involving use of a conductive metal insert in a gap of the bridge to serve as means for enhancing a fringing flux exteriorly of the gap, is termed "single-side" detection or "single-side" technique because the fringing flux produced by the bridge can be used to inspect the sample from one side of the sample. Further, the modification reduces the volume of the sample being scanned to fractions of a cubic inch. It is possible to detect cracks near rivets in aircraft wings with a bridge which is less than a cubic inch in volume through the use of this modification. The effect of this modification, further, is to move all the flux in a magnetic gap carrying a time-varying magnetic field completely out of the gap and into the fringe field.

Thus, single side detection utilizing magnetic bridge devices according to the invention can be carried out for nondestructive evaluation of variously configured structures and materials of ferrous or non-ferrous metal. The evaluation will reveal cracks, pre-crack or residual stress, surface flaws and volume voids or anisotropies.

Use of the invention is not limited to the evaluation of materials along planar surfaces. A specific modification of the above-described magnetic bridge devices, as disclosed in said patents, provides a device embodiment which may be inserted within a tubular structure, such as pipe, for detecting flaws within the pipe or other structure. In certain critical applications of pipe or other tubihg such as used, for example, for carrying high pressure steam within nuclear power plants and for use in heat exchangers in such plants, it is important to locate flaws such as within the walls of iron pipe. A device of the present invention is inserted solely within such pipe. The device, as configured for this use, includes driving and sensing legs which define respective axes which intersect the symmetrical axis of elongation of the structure and which are, themselves, mutually perpendicular, being preferably spaced apart along the axis of elongation to introduce within the walls of the structure four effective arms of the magnetic bridge. Magnetic flux is produced in the driver leg of the bridge, and the design causes the time-varying magnetic flux thus produced to divide into quadrants within the pipe walls. These quandrantal components are compared to each other by a sensing or signal leg of the bridge, and if the flux in the quadrants does not balance, a time-varying flux is induced in the sensing leg. It is sensed by a coil wound about the sensing leg, and the resultant electrical signal is analyzed for amplitude and phase of the fundamental and harmonic signals which appear, the phase being compared to the electrical signal which produces the flux in the driver leg of the bridge. The device is designed to produce components of magnetic flux which extend both circumferentially and axially within the walls of the pipe.

According to a further embodiment of the invention, a magnetic bridge device utilizing "single-side" technique is employed as an accelerometer, herein termed bridge-accelerometer by using a magnetic bridge to sense the position of an elastically suspended mass.

Accordingly, among the several objects of the inventions may be noted the provision of magnetic bridge devices of various configurations for carrying out nondestructive evaluation of ferrous and non-ferrous samples and structures, such as to detect cracks, pre-crack stresses, surface flaws, volume voids, anisotropies and other anomalies therein, regardless of the shape or size of the sample or structure, such as for the purpose of coin testing, pipe testing, surface testing, aircraft structure evaluation, and many other evaluative purposes; and which can detect hysteresis loop "signatures" such as can predictably and accurately reveal the characteristics.

It is further an object of the invention to provide such magnetic bridge devices which can be utilized for other evaluative and measurement schemes, including measurement of temperture changes of samples of ferrous or nonferrous metals regardless of size, shape or condition of motion of the samples; which can detect and/or measure thicknesses of laminants on ferrous or non-ferrous metals (such as coins and other clad or laminated metals, whether the laminants or surface coatings thereof are metallic or non-metallic; which can be utilized for measurement of the dimensions of samples of ferrous or nonferrous metals and of indentations or imprints in such samples, such as, for example, on coinage or on ruled objects, such as metal rulers.

Among other objects of the invention are to provide magnetic bridge devices which can be utilized for the measurement of distance or angular displacements with devices such as linear or angular transducers, such as for vibration detection or for motion detectors, and specifically, as an accelerometer. It is also an object to provide magnetic bridge devices which can be utilized for the detection of metallic objects or variations in displacements of metallic objects such as on assembly lines or in intrusion alarm systems.

Other objects and features will be in part apparent and in part pointed out hereinbelow.

BRIEF DESCRIPTION OF THE DRAWINGS

Corresponding reference characters indicate corresponding elements throughout views of the drawings.

DESCRIPTION OF THE PREFERRED EMBODIMENTS

Figures 1, 2, 3A, 3B, 4A, 4B:
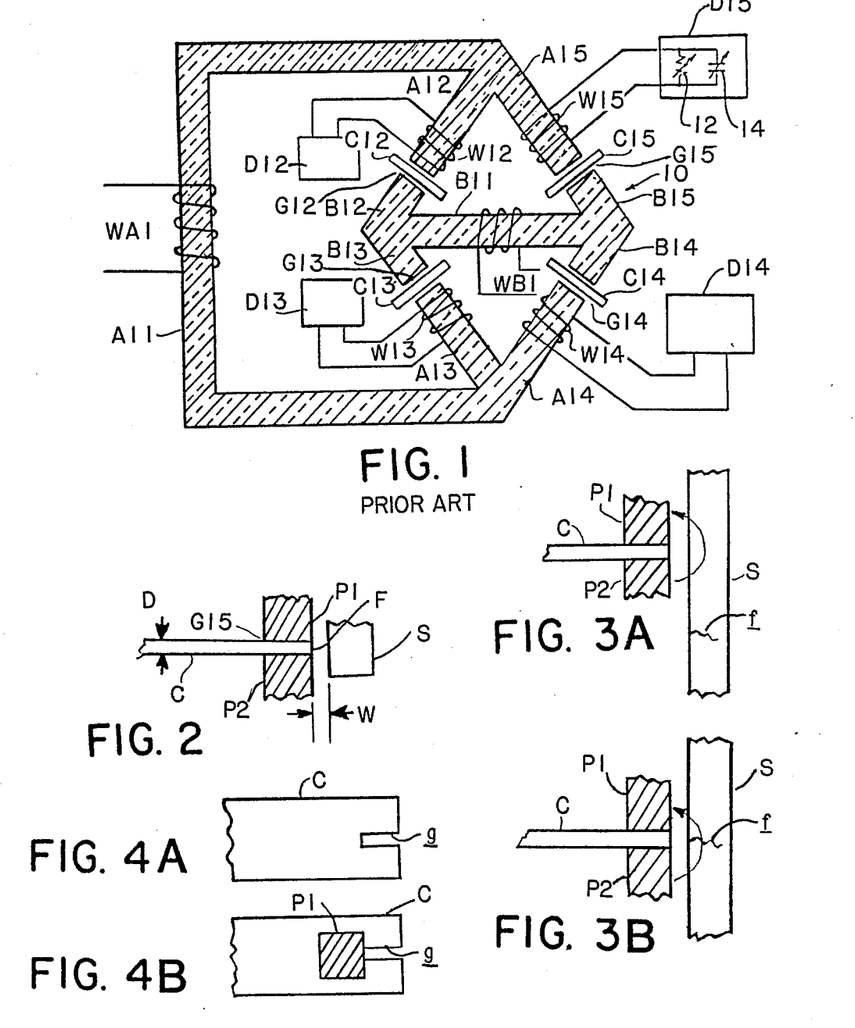
FIG. 1 is a schematic diagram of a magnetic bridge and associated circuitry in accordance with the prior art.
FIG. 2 is a simplified, fragmentary view of pole pieces of a magnetic bridge device as provided with a conductive insert between them in accordance with the invention for magnetic evaluation of an adjacent sample.
FIGS. 3A, 3B, and 3C together represent fragmentary views similar to FIG. 2, depicting magnetic evaluation of a sample for flaws by magnetic bridge devices of the present invention.
FIGS. 4A and 4B are fragmentary illustrations of conductive insert and associated pole configurations in accordance with the invention.

Referring to FIG. 1, a magnetic bridge circuit 10 of the type illustrated in the aforesaid Zinke U.S. Pat. No. 3,534,253 serves to explain the present invention.

Magnetic bridge circuit 10 includes integral portions A11, A12, A13, A14 and A15. The bridge also includes integrally connected portions B11, B12, B13, B14 and B15. Portion A11 is the input leg of the bridge and has an input winding WA1 mounted thereon. Winding WA1 is connected to a changing or varying current source which generates a varying flux in the core structure. In similar manner, leg portion B11 is the output leg portion and it has an output winding WB1 mounted on it. Output winding WB1 responds to changes in the condition of the flux in the bridge.

Output winding WB1 is connected to a suitable output circuit, device or other output means for measurement of the magnitude and phase of the signal induced in output winding WB1 and for comparison of its phase relative to that of a time-varying input signal.

Thus, it will be seen that the bridge includes an input leg, an output leg and effectively four arms. For example, a single arm may be regarded as formed of portions A12, B12, for example, and with each arm having a respective gap G12, G13, G14 and G15 in which are positioned gap insert elements C12, C13, C14 and C15 for gap-coupling between the adjacent ends of the bridge portions defining the gaps. However, the ends of the arm-defining bridge portions so illustrated may in some cases be in direct contact or formed integrally, as for the purposes stated in said Zinke U.S. Pat. No. 3,534,253.

Each of portions A12, A13, A14 and A15 has a respective winding or coil W12, W13, W14 and W15 mounted thereon. These windings are connected, respectively, to passive circuits such as circuits D12, D13, D14 and D15. Each of the passive circuits includes adjustable passive elements which are used for nulling the circuit in order to produce a minimum output on winding WB1 when the bridge is in balanced or null condition. A typical passive resistive-capacitive (R-C) circuit is shown in block D15 and includes a variable resistor 12 and a variable capacitor 14 connected in parallel. Other combinations of passive circuit elements can also be used in these blocks and it is usually desirable to include both resistive and reactive elements. By adjusting the elements in circuits D12-D-a null condition is produced, as aforesaid, when the output on winding WB1 is a minimum. The null condition is produced by the effect the passive circuits have on the real and imaginary components of the flux in the respective arms of the bridge circuit. This simultaneously changes the phase and magnitude of the flux in the arms and hence also produces the desired minimum flux condition in the output leg B11, and hence in output coil WB1.

By employing a time-varying or AC input source the reluctance becomes complex and the conditions and equations for balancing the bridge must take into account the fact that the reluctance is complex and that the reluctance has both real and imaginary components.

The magnetic bridge device thus to be generally utilized for the present invention may be constructed of H-shaped pieces as described in said Zinke U.S. Pat. No. 3,534,253, which pieces are of ferrite material having the desired flux concentrating and magnetic characteristics, although other flux concentrating materials may be utilized. Variously shaped members may be utilized for forming bridges in accordance with the invention, however.

Figure 3C:
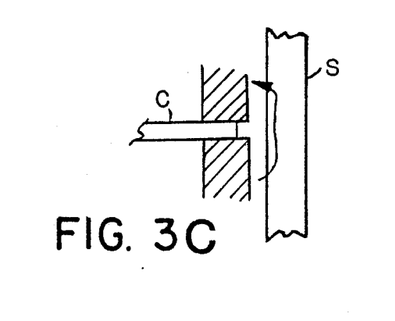

Throughout the drawings, material having a magnetic permeability greater than unity, such as ferrite or other ferrous materials, is illustrated by light cross hatching Referring to FIG. 2, bridge 10 is modified in accordance with the present invention by configuring one of the bridge arms for sample evaluation by introducing within at least the gap-forming poles of the sample-evaluating leg, e.g., gap G15, a gap insert C of electrically-conducting metal such as copper or aluminum. Insert C has dimensions such that it usually extends well beyond the poles P1, P2 except that outer edge of insert C provides a flush face F along at least one side of the gap. This arrangement enhances fringing of the flux across the gap to such an extent that it provides a fringing field only on the side of the gap across face F, as the total flux is removed from the gap because of the circulating (or eddy) current produced within the conductive insert. The magnitude of the circulating current is dependent upon the conductivity of the insert which, in turn, is dependent upon the thickness D of the insert. From Lenz's Law it is known that the circulating current in the gap insert will produce a magnetic field which opposes the inducing field so that, by the theory of superposition, the field in the center of the gap will decrease as the two magnetic fields add. With appropriate gap width, being the same as the thickness D of the gap insert, most of the inducing field is inside the gap. That is, there is a very small fringe field. However, because the eddy current follows the outside dimension of the insert, it produces a field inside the gap and outside the gap. Outside the gap there is no inducing field to cancel the induced field so that as the conductivity of the insert increases (i.e., as D increases) the field inside the gap goes to zero and the field outside the gap increases. The net effect is accordingly to move the fringing field from within the gap to outside the gap and thus along face F. Accordingly, the bridge has been modified by modifying the insert within the gap in order to move the flux from inside the gap to outside the gap where it becomes a fringing flux. In many applications of the present development, the gap insert may be of greater dimensions than the gap and so extend beyond it. But in other uses, a gap of the bridge may only have its area partially filled (FIG. 3C). Thus, in any event, the gap insert at least partially fills the gap. But if partial, then the gap so partially filled includes at least one shim of electrically conductive and/or magnetic material for balancing of the bridge.

For utilization of the bridge so modified to provide a single-side detector, a sample S is positioned adjacent face F by a distance W. If the sample is ferrous, the magnetic field will be attracted to the sample and alter the flux causing a change in the off-null signal of the bridge. If the sample is nonferrous, then magnetic field lines will be squeezed between the sample and the sample-evaluating gap, again altering the off-null signal of the bridge. The "squeezing" occurs because of the Faraday effect and Lenz's Law. In either instance, the sample affects the field so that a signal results from the presence of the sample, and may be detected in the sensing leg B11 by sensing coil WB1. Moving the sample back and forth in a direction normal to the gap alters the off-null signal of the bridge, permitting the bridge to be used as a linear transducer measuring the distance W.

Because of these principles of operation, the bridge can also be used in other ways taking advantage of the capability for measuring the distance W. If the sample is driven, for example, by changing air pressure, the magnetic bridge device may then be used as a manometer or a microphone. If sample S is a rotating shaft having eccentricity, and W represents the distance between the sample and the gap face F, the eccentricity of the shaft can be readily determined. Further, if the eccentricity is appropriately asymmetric, the bridge can be used as a tachometer. Further, if sample S is a vibrating device, and the bridge is placed at an average distance W from such vibrating device, the bridge will measure the rate of acceleration of the device.

To further illustrate methods of usage and applications of the bridge, it may considered that sample S is a metal reed fastened to the same mechanical ground as the bridge. If the whole configuration is then vibrated, in time the reed will vibrate with respect to the gap at the same rate as the driving frequency and the bridge signal will now indicate the frequency. If the space represented by W is filled with material having different electrical characteristics from the sample, then the off-null signal from the bridge can be made to be representative of the thickness of that material whether the material is nonconducting, such as a carbide layer on a tool, or conducting, such as the cladding on the copper insert of coinage. By proper choices of frequency, the bridge can be made to "read" the fact that a coin has printing, one of the basic differences between genuine coins and most spurious coins (commonly called "slugs"). A great many, if not most, slugs have flat sides. The upset edge of a real coin can be registered on the gap so that W becomes the airspace generated by the printing on the coin. Slugs usually do not have such printing. Printing on some coins is frequently of a different average W as compared to other coins of essentially the same dimensions and electrical conducting. Choices of several frequencies can indicate both printing and cladding and provide a fool-proof test for coinage in automatic apparatus using very inexpensive circuitry.

The single-side bridge can be used to detect flaws such as precrack and other residual stress, cracks, surface cracks, voids, metal fatigue, etc. in the manner shown in FIGS. 3A and 3B. First the bridge is nulled as shown in FIG. 3A. Then the sample S is moved. If a flaw simulated by crack f has occurred, the flux lines in the sample are interrupted when within the fringing field, as shown in FIG. 3B or altered in some manner affecting phase and amplitude at the bridge output. While the basic physics of the flux paths differ between ferrous and nonferrous metals, the indication of the bridge is the same, that is, an off-null signal in the presence of a crack, void, pre-crack or residual stress, or other anomalous feature.

The magnetic field of the embodiment shown in FIG. 3A will enter and leave the sample perpendicular to a plane. The net flux through such plane is zero because the flux both enters and leaves. By Faraday's Law, no circulating (eddy) current will be induced in that plane. A circulating current induced in that plane would spread throughout the sample dimensions as such a circulating current spreads with an unmodified bridge in accordance with Zinke Patent 3,534,253. The only circulating currents which can be induced in sample S outside the region near the insert must be perpendicular to the plane discussed above. These circulating currents will be limited in their depth of penetration from that plane by the skin effect. The skin effect can be controlled by the operator of the bridge through choice of the frequency of the time-varying signal driving the bridge, i.e., as provided across winding WA1. Thus, the volume of sample S which is being searched is limited to dimensions controlled by the size of the conductive metal insert and the frequency of the bridge which is contrary to the volume inspected by an unmodified bridge as in said Zinke Patent 3,534,253, which is essentially uncontrollable by the operator except as to depth from surface. A single side bridge in accordance with the present invention allows the operator to sharply limit the area of a sample being evaluated, such as for flaws, printing and so forth.

For very high sensitivity measurements where very large magnetic fields are desired, i.e., where it is desired to concentrate the flux in a very small area, an insert C such as that in FIG. 4A having a narrow slot or gap g can be used where the base of the slot shown in the insert fits just at the point opposite from the sample when the poles and the insert are combined as shown in FIG. 4B.

Figures 5A, 5B:
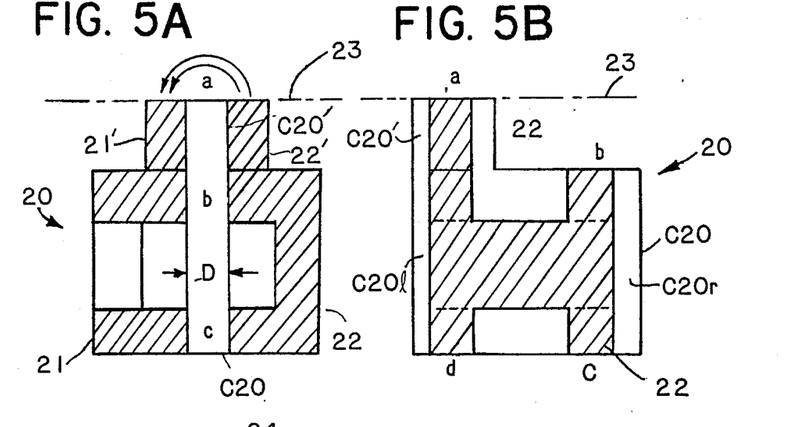
FIGS. 5A and 5B are respectively front and side views of a magnetic bridge device in accordance with the invention providing single side detection in accordance with the present disclosure.

Referring to FIGS. 5A and 5B, an embodiment 20 of a magnetic bridge utilizing the single-side technique is illustrated, wherein the ferrite pieces of the bridge are of generally H-shaped configuration to provide a left bridge piece or half 21 and a right half or bridge piece 22 which are located on opposite sides of a conductive metal insert C20 of generally L-shaped configuration. The insert may, for example, be of copper and to which the bridge pieces are secured by suitable adhesive.

For simplicity, the various windings upon the core have not been illustrated but will be understood to be utilized in accordance with the foregoing description and the teachings of Zinke Patent 3,534,253 which discloses H-shaped pieces, as of ferrite. Instead of copper, any conductor or superconductor may be used for insert C20. In any event, the bridge pieces are elongated at an upper end to provide sample-evaluating pole portions 21, 21', 22' having outer extremities which lie in a plane 23 which is also coincident with the upper extremity of insert C20. In plan (as evident in FIG. 5B), insert C20 is of relatively greater width than corresponding portions of the bridge halves 21, 22 whereby to provide marginal portions C20*l* and C20*r* extending beyond corresponding surfaces of the bridge portions 21, 22. The insert C20 is provided with an upper extension C20' which extends between the upper extensions 21', 22' and similarly is of relatively greater width. Thus, between the bridge leg extensions 21', 22' there is provided a gap a between the upwardly extending bridge leg portions 21', 22'. The gap is used for detection, whereas three other gaps b, c and d are similarly formed across corresponding portions of insert C20 to provide corresponding magnetic paths for balanced operation of the bridge. Generally, the sample-evaluating gap a is used for detection and the other gaps b, c and d are used for rough nulling of the bridge. Detection takes place above plane 23, across which a fringing field extends generally as shown in FIG. 5A. If desired, an aluminum face plate may be fitted around the upwardly extending portions 21', 22' and C20' such as to provide a convenient surface across which samples may be moved and/or for shielding the bridge from unwanted samples. Such face plate may be closely conformed to the periphery of elements 21', 22' and C20' will be insulated electrically from at least portions of the gap insert. Such assembly may be secured by appropriate adhesives, such as epoxies.

Figure 6:
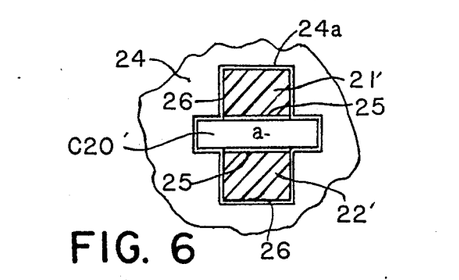
FIG. 6 is a fragmentary plan view of portions of the bridge device of FIGS. 5A and 5B as exended through an apertured face plate.

Thus, there is formed a single-side bridge providing gap a for detection. Samples may be moved across gap a as shown in FIGS. 2, 3A and 3B. It will be evident that the surface across gap a is entirely flat and, if member 21' and 22' extend into a plate, as shown in FIG. 6, in accordance with the above-described modification, a polished surface may be provided. However, the surface of the gap can be shaped to conform to the particular aspect of the sample being examined. Of course, the thickness D of the insert may be varied in accordance with the usage to be made of the bridge and the material.

In FIG. 6, a face plate 24 having an aperture 24a receives the bridge extension portions 21', 22' and the insert portion C20' which separates said portions to form gap a. In this view, thicknesses are exaggerated to show a layer of adhesive such as epoxy, indicated at 25 which adheres the bridge portions 21', 22' and gap insert C20' together and with the whole assembly then being secured in aperture 24a by a further layer 26 of adhesive, such as again of epoxy type. The epoxy layers also provide electrical isolation, serving as means for providing electrical isolation between the conductive gap insert and at least portions of the face plate. The face plate may be a wall or otherwise part of an electrically conductive enclosure completely enclosing the bridge device for providing electromagnetic shielding.

Figure 7A:
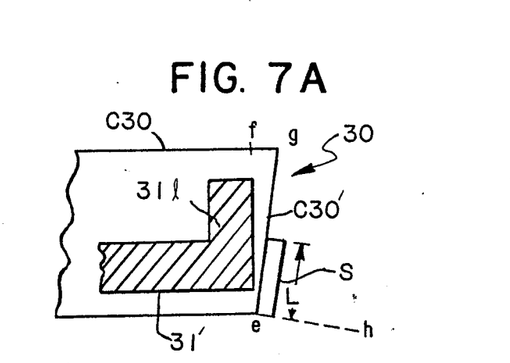
FIGS. 7A and 7B are respectively fragmentary plan and end views of portions of pole and insert elements of another bridge device embodiment.
Figure 7B:
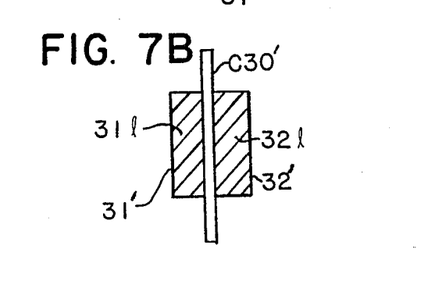

Referring then to FIGS. 7A and 7B, a portion of an embodiment 30 of a single-side magnetic bridge of the invention is illustrated. In this version, L-shaped poles are used, being designated as 31', 32' similar to the pole extensions 21', 22' of the version of FIG. 5A, but instead having also L-shaped portions 31*l*, 32*l*. Between these pole portions of the bridge, which otherwise is generally of the configuration such as shown in FIGS. 5A and 5B, there is provided a conductive metal insert C30, as of copper. The outer end of insert C30 forms an angle feb to provide an outer linear edge C30' of the insert against which a sample S may be positioned, said sample having a length L which, if to be measured, can be registered on the line eh. As shown, the sample is registered on eh. If L changes, the flux path between the pole portions 31*l*, 32*l* change so that the off-null signal of the bridge changes, indicating a change in the dimension L of sample S. Accordingly, the bridge may be used to provide a very sensitive measurement of the length of the sample, such as in measuring or selecting dimensions of parts used for assembly, in sorting, and other dimensional evaluation. The spacing between the pole faces and the gap insert varies along the length of the gap since the outer ends of the pole pieces 31*l*, 32*l* lie along one plane axis or in one plane and insert outer edge ef lies along another axis or in another plane skewed relative to the first by angle feg.

The arrangement of FIGS. 7A and 7B, by appropriate pole geometry, may be used for evaluating, among other characteristics, the diameter of coins. Among such characteristics are the existence of printing. By choice of frequencies, a bridge of the invention may indicate both printing and cladding, thereby provide full-proof test for coinage in coin evaluation apparatus. Slugs may readily be rejected by the sensitive magnetic evaluation provided. The dimensional evaluation permitted by this arrangement can be used for "reading" types of coins.

Figures 8A, 8B:
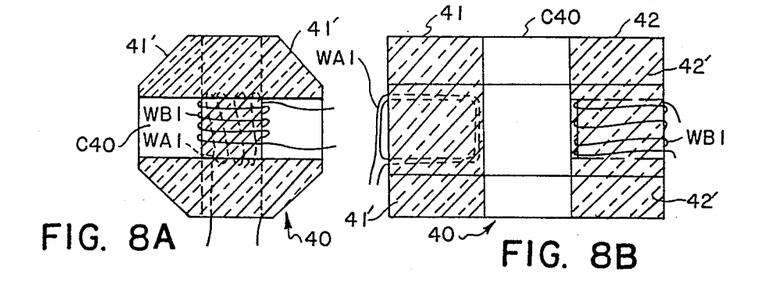
FIGS. 8A and 8B are respectively side and end views of a magnetic bridge device of the invention as utilized for the construction of an accelerometer.
Figure 8C:
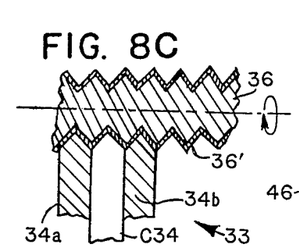
FIG. 8C is a bridge device for evaluating a threaded structure.
Figure 8D:
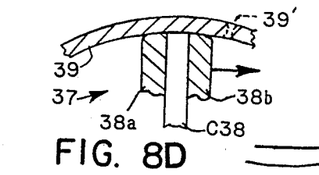
FIG. 8D is a bridge device for evaluating a cylindrical surface.

Referring to FIG. 8C, a bridge device embodiment 33 having gap-defining pole pieces 34a, 34b and a conductive insert C34 between them for enhancing the fringing flux may be used for evaluating a structure 36 such as a thread tap having carbide coating 36', such as to determine the uniformity and thickness of the coating. In this embodiment, both the pole pieces and gap insert have outer surfaces conforming to the threaded aspect. The evaluation may occur as the sample is rotated as indicated. In FIG. 8D, an embodiment 37 of the bridge device has pole pieces 38a, 38b and a conductive insert, C38 having outer gap-defining surfaces lying all within a cylindric surface for evaluating a tubular structure 39 by movement along its surface as illustrated by arrow. The technique may be used to magnetically locate a weld 39' which would not otherwise be visual. These embodiments are merely indicative of various device configurations having nonlinear pole and insert geometry for evaluating variously shaped samples with nonlinear surfaces.

In such usages of a single side bridge, as herein described, data "signatures" are sensed in the output leg of the bridge which are sufficiently unambiguous to allow identification and characterization of defect morphology in metal samples and of lift-off of the bridge. A combination of scanning patterns is obtainable by utilization of bridges of the invention to provide such a "signature", as by measurement of bridge output variations in the presence of a flaw or liftoff of the sample, as measured, for example, by the electrical parameters (e.g., resistance or capacitance) necessary to renull the bridge at particular frequencies, or by measurement of the amplitude and phase in the output leg. The variation of such parameter with translational distance of any one of these variables can be termed such a "scanning pattern". Among the several kinds of patterns presented by the bridge of this invention are the following:

a. A central peak which seems to respond primarily to surface conditions of the sample.

b. Satellite peaks which seem to respond primarily to subsurface conditions c. Directional response to the angle between the scan and the flaw which can be made on the basis of width of the central peak.

d. Individual scanning patterns for amplitudes and phases of the fundamental and harmonic frequencies which are impressed on the bridge through the input signal.

e. Individual scanning patterns for amplitudes and phases of harmonics which are generated in the sample.

Referring now to FIGS. 8A-8B and 9A-9B, a version 40 of the bridge is illustrated which is utilized for the purposes of constructing an accelerometer, which is designated in its entirety by reference numeral 40'.

Accelerometers are transducers which typically measure the acceleration of the mechanical structure to which they are attached. If the structure moves periodically, these transducers will indicate the frequency of the motion. The information which is gathered under these circumstances, acceleration and frequency, can be used in a technique called "modal analysis" for the nondestructive evaluation of future structure integrity. Mechanical structures which can be evaluated through modal analysis are air and space frames, off-shore oil rigs, highway bridges, buildings in earthquake zones, and the like. In most of these applications a complete modal analysis requires the deployment of a large number of accelerometers on a permanent basis.

A more complete modal analysis of an oscillating mechanical structure can be carried out if the amplitude (rather than the acceleration) of the structure motion is measured as well as the frequency. Accelerometers typically in use do not generate information which would allow the amplitude to be calculated. In fact, this information is usually obtained by placing a displacement transducer on a reference frame which is stationary with respect to the structure and measuring the distance between the frame and the structure. Such a device is called a contact transducer or contact accelerometer. Under many circumstances, for example, a flying aircraft, the use of a contact transducer is impossible. If the accelerometer contains among its elements a displacement transducer, it is possible to obtain the amplitude of the structure oscillations from the information the accelerometer generates.

The most common accelerometers are based on signals generated by piezoelectric crystals which serve as acceleration detectors. These devices do not allow a calculation of structure oscillation amplitudes. Further, these devices are expensive so that deployment in large numbers may substantially affect the cost of the structure. These devices also have a high impedance which interferes with the electrical signals generated under low-amplitude, low-frequency conditions. Cables to the devices should be shielded adding to the mass and expense of the devices.

Figures 9A, 9B:
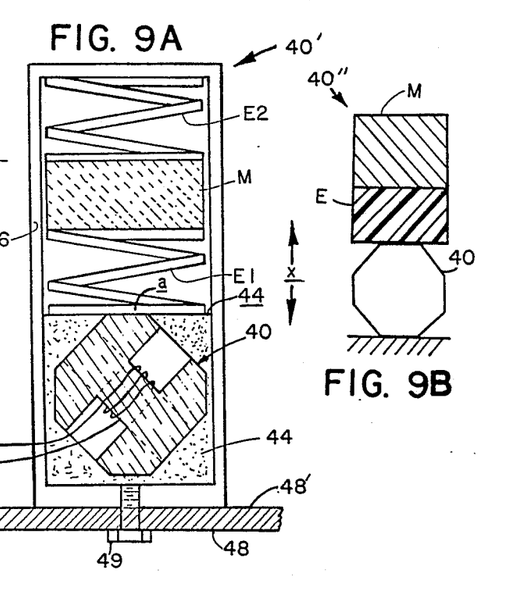
FIG. 9A and 9B are vertical cross-section illustrations of accelerometers constructed with the magnetic bridge device of FIGS. 8A and 8B.

Single-side bridge 40 of FIGS. 8A and 8B is easily configured into a displacement transducer for inclusion as an element of accelerometer 40' shown in FIG. 9A. In this configuration it is competitively sensitive in output volts/inch with all other displacement transducers. Bridge 40 senses the distance between itself and a conducting and/or a ferritic sample, namely a mass M. If an elastic element is used as resilient support in the form of one of a pair of compression springs E1, E2, to interconnect the bridge and the sample and one or the other allowed to oscillate freely, the device constitutes an accelerometer with the special capability of being able to measure the amplitude of structure vibrations as well as frequency. The accelerometer so constructed about the same size as piezoelectric accelerometers, about the same mass, but have a cost which is a factor of about 50 less. The output impedance is so low that shielded cables are not normally required. Power requirements are modest, of the order of watts for a 20 KHz signal.

More specifically, bridge 40 is formed of H-shaped halves 41, 42, each having chamfered corners as at 41', 42'. A conductive metal gap insert C40 is provided between the two halves, and similarly has chamfered corners. The windings WA1 and WB1 of the winding and driving legs are representatively illustrated. Referring to FIG. 9A, bridge 40 is incorporated into accelerometer 40' by being imbedded within a block 44 of epoxy with the bridge oriented so that chamfered faces of the bridge are oriented horizontally to provide exposure thereof at the upper horizontal face 44' of the block of epoxy for presentation thereby of a gap a so that the fringing field across said gap produced by the conductive metal gap insert C40, which may be of any good electrical conductors such as aluminum or copper, will either pass through mass M or otherwise produce variation in the fringing flux so as to be reflected in the output leg of the bridge. The mass may be formed of ferritic material as noted. Accelerometer 40' includes a suitable and cylindrical enclosure 46 secured to a surface 48 upon which the accelerometer is to be utilized for measurement of the acceleration experienced in a direction normal to the surface 48' of said structure 48. Merely as an illustration of one method of securement, a bolt 49 is threaded through structure 48 into enclosure 46. By virtue of the elastic support of spring members E1, E2, mass M is free to move up and down within the housing 46 of the accelerometer so that the bridge will measure the distance x shown. A bridge output which is linear over a region of expected variations of the displacement variable x will be obtained. Although the bridge output might be expected to be nonlinear over sufficiently great variations of x, by optimum selection of the spring constant of the elastic elements E1, E2, movement of the mass M can be expected to result in bridge output which is a linear function of x within the region of interest.

Various other materials may be substituted for the mass M, such as aluminum or may be a combination of nonconducting materials or masses, which may be wrapped or otherwise covered or coated with conductive metal as, for example, aluminum.

Referring to FIG. 9B, an accelerometer version 40" using bridge 40 is shown with mass M secured to bridge 40 by a resilient layer E of epoxy or other adhesive, which materials may be shown to have elastic properties such as to provide resilient support of mass M which thereby will be displaced by acceleration. The displacement is detected by bridge 40.

Referring now to FIGS. 10-15, the techniques of the present invention are utilized for the construction of a device for magnetically evaluating the integrity of the walls of ferrous tubular structures, such as steel or iron pipe, having the capability for detecting an anomaly which may be present along the length of such structure. Briefly, the design provides such nondestructive evaluation by being inserted solely within the pipe or other tubular structure. Magnetic flux is produced within the driver leg of a bridge which is constituted by the device together with the walls of the tubular structure, causing a time-varying magnetic flux to be divided into quadrants within the structure wall. Merely for purposes of convenience, the structure will be referred to herein as a pipe, but may, in fact, be any of various comparable tubular structures to be so evaluated.

In any event, the quadrants so induced within the pipe walls are compared to each other through the inclusion of a signal leg of the bridge. If the flux in the quadrants does not balance, time-varying flux appears in the signal leg. This flux induces an electrical signal in a coil wound about the signal leg, and the electrical signal is analyzed for amplitude and phase of the fundamental and harmonic signals which appear, where the phase is compared to the driving signal which produces the flux in the driver arm of the bridge. The device is designed to produce both components of magnetic flux which travel both radially and axially in the walls of the pipe.

Figure 10:
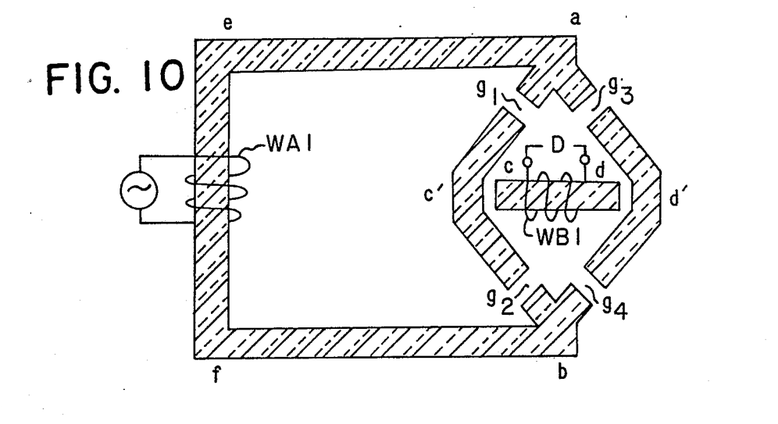
FIG. 10 is a schematic diagram of a magnetic bridge device illustrating certain concepts of the invention.
Figure 11:
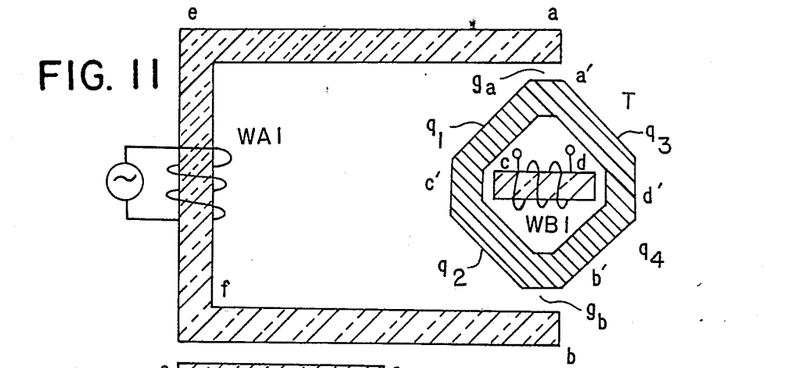
FIG. 11 is a similar schematic diagram showing a modified magnetic bridge apparatus illustrative of the invention.

Reference to FIGS. 10 and 11 aids in understanding the design of the pipe testing device. The basic design of the magnetic bridge is powered by time-varying magnetic flux is shown in FIG. 1. As in other views, light cross-hatching illustrates material having a relative permeability greater than unity such as ferrite. The configuration is analogous to an electrical bridge with the notable exception that time-varying magnetic flux is substituted for a time-varying electric current. The time-varying flux is produced by a time-varying electrical current in coil WA1 wound around the driver leg ef of the bridge. The gaps $g_1$, $g_2$, $g_3$, and $g_4$ together with any materials responsive to magnetic fields which is placed within the gaps and any electrical impedances attached to coils coupled to the arms (see Zinke Patent 3,534,253) effectively constitute what may be considered to be "magnetic impedances" in the respective arms of the bridge. Should these magnetic impedances balance, the flux in the four arms will balance, and no time-varying flux will appear in the signal leg cd of the bridge. However, if there is not a balance, time-varying flux will appear in the signal leg cd and will induce an electrical signal in the coil WB1 where it can be analyzed for amplitude and phase of fundamental and harmonic frequencies by a detector D. "Magnetic impedances" is not a term which is in widespread use. Any factor listed above as affecting the flux in any arm of the bridge has the capability of altering the net hysterisis loop of that arm. Over a cycle of alternating current, the flux circuit sweeps out the hysteresis loop. The average slope of the magnetic field versus the driving ampere turns (or its equivalent) represents the average permeability of that arm of the bridge. The average permeability is a measure of the energy stored in the magnetic circuit and is related to what may be considered the real part of the magnetic impedance, the reluctance. The area of the hysteresis loop is related to the energy dissipated in the arm of the bridge and would be related to the imaginary part of the magnetic impedance. This imaginary part of the magnetic impedance is as yet unnamed. Actually, until the advent of the magnetic bridge powered by a time-varying signal, there was no reason for such a concept (see, e.g. O. H. Zinke and Paul B. Jacovelli, Rev. Sci. Inst. 36, 916, 1965 or Zinke U.S. Pat. No. 3,378,969). Magnetic circuit theory is particularly difficult to formulate for the new device because the impedances do not appear as coefficients of derivatives in a simple linear differential equation such as with electrical circuit theory. In fact, if the theory is quantified, it appears that the appropriate equation will have to be a yet-unrealized nonlinear integral equation. Until such time, it is appropriate to think of the real part of the impedance as relating to energy stored in a magnetic circuit and the imaginary part of the magnetic impedance as the energy dissipated. The convention is opposite to that of an electrical circuit where the resistance is the real part of the electrical impedance.

To understand the theory of the pipe tester device, refer to FIG. 11 which shows adaption of the magnetic bridge apparatus of FIG. 10 for evaluation of a closed structure. There a generalized structure T, which may be of tubular formation, replaces the bridge arms. Structure T may be the walls of tubing or pipe. Here the gaps $g_1$, $g_2$, $g_3$, and $g_4$ have been eliminated and new gaps $g_a$, $g_b$ now exist between a and a', b and b'. Gaps also exist between c and c', and d and d'. In the positions shown, these new gaps do not affect the balancing of the bridge although they may affect the impedances which the driver and signal coils "see." There are still four bridge arms which are a'c', a'd', c'b', and d'b'. The driver leg is now seen to be the total length afeb. The signal leg remains cd. The manner in which a pipe can be made into a magnetic bridge can now be seen by comparing FIG. 11 to FIG. 12. The round pipe walls are now shown to be divided into the four arms a'c', a'd', c'b', and d'b' solely through the positions of the driver and signal legs of the bridge with respect to the pipe. Ideally, if these arms are of the same magnetic impedance, the flux within them will balance, and no signal will appear in the signal leg cd. Suppose, however, that, e.g., a gap or thickness variation is created between a' and d' through erosion, corrosion or a bad weld. Most of the flux will travel from a' to c' where it will divide with part of it going through cd and subsequently to b through d'b' while part of the flux goes to b through c'b'. Thus a signal appears in the signal arm cd.

Figure 12:
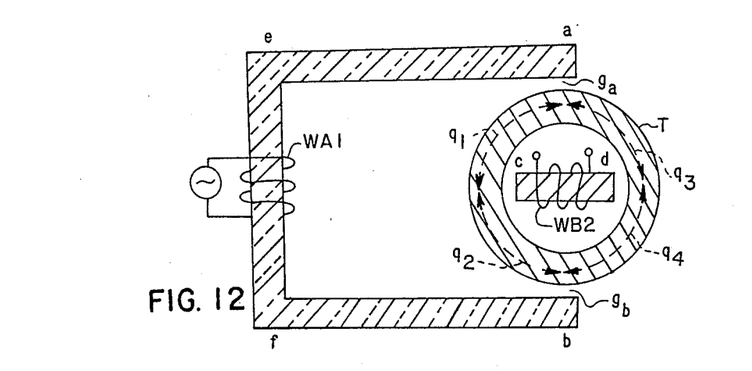
FIG. 12 is a similar schematic diagram of the magnetic bridge apparatus of the invention for magnetic evaluation of a tubular structure.

FIG. 12 represents the configuration for structure T as being cylindrical as in the case of pipe of steel or iron. Thus, magnetic bridge apparatus can be constructed in the generalized form shown in FIG. 12 to provide poles ab on opposite sides of the pipe for coupling magnetic field produced by the driver leg ef upon energization of coil caps WA1 because of gaps $g_a$, $g_b$ formed on opposite sides of the tubular structure T. A sensing leg cd within the tubular structure may be moved longitudinally along the length of tubular T as the poles ab similarly are moved and with the legs ef, ab and cd, all being generally coplanar as the bridge components are moved relative to tubular structure T thereby to introduce a magnetic flux in each of four quadrants $q_1$, $q_2$, $q_3$ and $q_4$. The imbalance in any one of the quadrants caused by an anomaly in the walls or structure of the tubular element T will cause an imbalance to be detected by sensing coil WB2.

Figures 13, 14, 15:
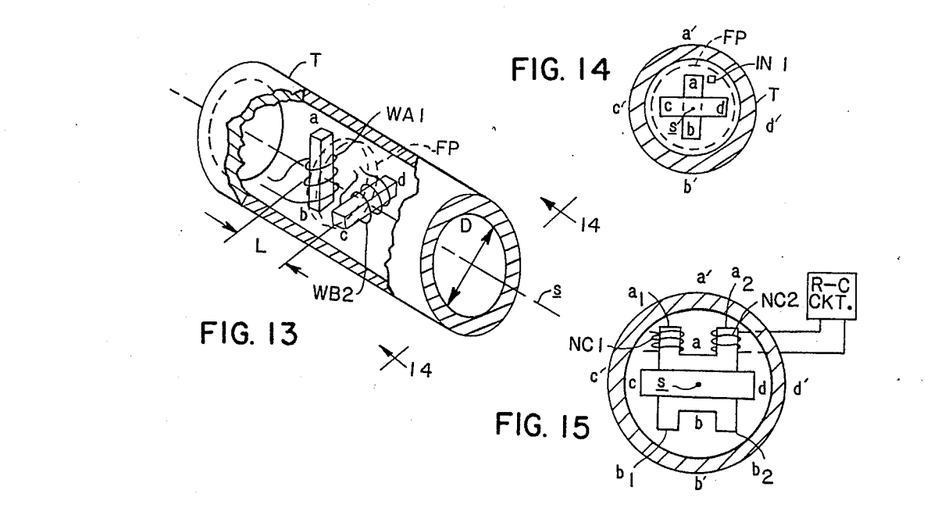
FIG. 13 is a perspective view, partially fragmented, depicting elements of a magnetic bridge device of the invention for evaluating a tubular structure, as the device is preferably configured.
FIG. 14 is a lateral construction of the apparatus and structure shown in FIG. 13, as taken generally along line 14—14 thereof.
FIG. 15 is a similar cross-section illustrating a modified version of the magnetic bridge device of FIG. 13.

In the configuration of FIG. 12, part of the bridge is inside the pipe and part of it is outside of the pipe. Referring to FIG. 13, this problem can be solved by reducing the distances af and eb to zero so that f now becomes a and e now becomes b. The distance ab is shortened until it is smaller than the diameter D of the pipe or other structure T. The driver arm, which is now ab, is then placed perpendicular to the signal arm and perpendicular to the axis of symmetry of the pipe. The axis of the signal arm pole cd is already placed essentially perpendicular to the symmetrical axis of elongation of the pipe. The axis of driver arm pole ab is then placed some distance L along the axis of elongation s behind the signal arm cd as shown in FIGS. 13 and 14 whereby the quadrantal flux components will be both circumferential and axial within the walls. A field confinement piece FP of highly-conducting metal, which is cylindrical in shape and has an outer diameter of somewhat less than the inside diameter D of the pipe, is used to keep the magnetic flux from following a path other than that in the pipe. The circumferential and axial flux paths thus formed allow the device to test the integrity of both paths in the pipe wall simultaneously. The outer ends of poles ab, cd are pair wise radially equidistant from axis s.

Nulling a bridge such as that depicted in FIGS. 13 and 14 presents special problems in that coils cannot be wound around the arms of the bridge as in Zinke U.S. Pat. No. 3,534,253. The arms of the bridge are now the walls of the pipe. Rough nulling can be done, however, by rotating the axis of driver leg ab with respect to the axis of signal leg cd until a null appears on the signal leg. Thus, in practice, the structure holding these legs allows rotation of one axis with respect to the other even though the axes are otherwise essentially perpendicular.

Such rough nulling, however, is important because the device may be driven with frequencies of the order of 10 Hertz, and the electrical impedances which must be attached to null coils to null at these frequencies could otherwise be enormous to accomplish rough nulling. Fine nulling can be accomplished as shown in FIG. 15 where leg ab has ends which have been bifurcated, being divided respectively into stubs $a_1$, $a_2$ and $b_1$, $b_2$ as depicted. Null coils $NC_1$, $NC_2$, etc. can be wound on one or more of these stubs and electrical impedances, such as the resistive-capacitance circuit shown therein, attached to these null coils to achieve nulling, that is, a minimum signal in the arm cd. At least one null coil could be used as a minimum. In addition, rough nulling can be accomplished by placing electrically-conducting or magnetic materials either to the right or the left of the ends of either the signal leg at c or d or the driver leg at a or b. Such a shim or insert is shown to the right of a on the driver leg in FIG. 14 as $IN_1$.

The electrical signal produced by this magnetic bridge device can be rich in information. In fact, use of all the potential information which can be generated by the device can be used to identify from the data the specific flaw which produced a deviation from null across the signal leg. There are two harmonic effects present: One of these is produced by driving the bridge across coil $C_1$ with a signal rich in harmonics and analyzing the phase and amplitudes of the fundamental and harmonic frequencies of the signal as has been suggested for electrical bridges in Zinke U.S. Pat. No. 3,059,749. The other effect is, however, quite unexpected and goes to the nonlinear nature of magnetic circuits. If the bridge is driven with a fundamental frequency which has harmonics which are essentially not detectable, harmonics can still be detected in the output signal of the magnetic bridge. These harmonics are generated by the driving of the hysteresis loop with a pure signal. Normally, they cancel, but if a flaw appears in one arm (quadrant), the hysteresis loop is altered and the harmonic content actually generated in that arm is altered and the imbalance appears across the signal leg. The difference between this effect and the effect previously suggested in by Zinke U.S. Pat. No. 3,059,749 is that the harmonics are actually generated in the bridge arms.

It is possible to utilize both these harmonic effects by adjusting the harmonic content of the input signal so that is is about the same order of magnitude as the arm-generated harmonics so that the superposition of these effects can be seen in the output. Another way of utilizing these two effects is to drive the bridge with harmonic-free and harmonic-rich signals in an alternating fashion and comparing the two types of signals thus generated.

Referring now to FIGS. 16–18F, a specific device embodiment 50' for pipe testing is illustrated. The device incorporates the magnetic bridge techniques of FIGS. 13–15 and may be used for evaluating any of various tubular pipe structures or pipe-like structures of circular shape. Device 50 is sized for fitting snugly within the inner diameter of the pipe or other structure T (as shown in phantom) to be tested. In such usage, device 50 is propelled through the pipe by suitable means, such as by cable drive. For example, structure T may be the bore of an oil well drill pipe into which device 50 is lowered by cable, the device being connected with driving and sensing circuitry by electrical leads extending along such cable.

Figures 16, 17A, 17B, 17C, 17D, 17E, 17F, 17G, 18A, 18B, 18C, 18D, 18E, 18F:
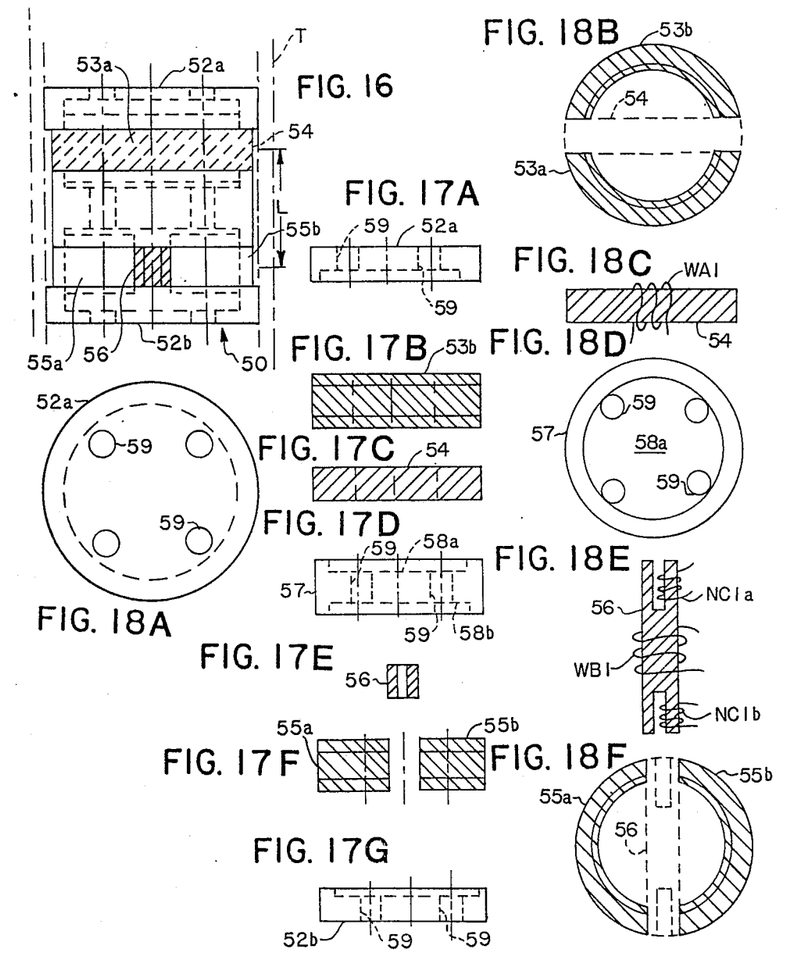
FIG. 16 is a side elevation view of a magnetic bridge device of the invention for evaluating a tubular structure such as a pipe from wholly within the structure.
FIGS. 17A–17G together are individual side views of elements of the apparatus of FIG. 16.
FIGS. 18A–18F are individually top plan views of elements of the device of FIG. 16.

Device 50 is of generally cylindrical shape, and includes at opposite ends, end plates 52a, 52b of disc-shaped cylindrical configuration. The end plates may each be of stainless steel and serve both to provide high strength structural protection for the device and also for knocking off any rough parts or projections on the inside of pipe T as the device travels through the pipe. Means for pulling the device through the pipe may be attached to the end plates.

Referring also to FIG. 18B, at 53a, 53b are designated two C-shaped parts for positioning the driving leg piece 54 of the bridge. Parts 53a, 53b are located on opposite sides of the driving leg which extends transversely of the device between the walls of the pipe for inducing a magnetic field within the walls of the pipe. The driving leg 54 is in the form of a ferrite rod of rectangular shape. Although not shown in FIG. 16 for simplicity, a driving winding WA1 is wound about the driving leg (FIG. 18C) to be driven by a suitable AC voltage source. Similarly, at 55a, 55b are shown C-shaped parts for maintaining in position a ferrite rod sensing leg piece 56 which also is of rectangular cross-section. However, as shown in FIG. 18E, the driving leg 56 is notched at opposite ends to provide bifurcated end stubs about which are wound nulling coils NC1a, NC1b as shown in FIG. 18E, to representatively show the manner of providing fine nulling of the bridge in accordance with FIG. 15. The leg positioning parts 53a, 53b and 55a, 55b are spaced apart by a field confinement piece 57 of cylindrical configuration, provided on its opposite faces of cylindrical recesses as at 58a, 58b for providing additional spacing within the device. Similarly, the end pieces 52a, 52b are cylindrically recessed on their inner faces for additional space within the device for windings and connection of wiring, as for null coils and the driving and sensing coils. Field confinement piece 57 is preferably of aluminum, being thus electrically conductive for causing the magnetic field established by driving leg 54 to be confined substantially entirely within the walls of structure T. Thus, it will be apparent that, in plan, field confinement piece 57 will be shaped in substantial conformity to the sectional shape of the structure T which is, in this instance, circular. The thickness of field confinement piece 57 along the axis of structure T is selected for defining an appropriate length for the flux to pass within the quadrants of the pipe as established by the relative positioning of the driving and sensing legs 54, 56 which are thus spaced apart by a distance L. Apertures, as at 59 are provided through the various pieces while receiving electrically insulated threaded rods or machine screws, etc. for maintaining the assembly in secured position as well as permitting attachment of means for propelling the device through structure T. The driving and sensing leg pieces 54, 57 may be other than linear.

Figure 19:
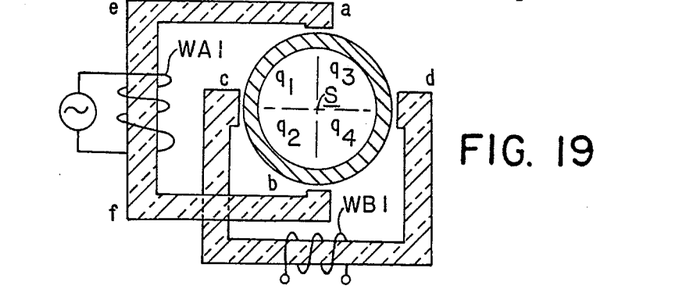
FIG. 19 is a schematic diagram illustrating magnetic bridge structure for evaluating a tubular such as a pipe from wholly outside the structure.

Referring to FIG. 19, an embodiment of the invention is schematically illustrated as configured for evaluating a tubular structure T from wholly outside the structure. A driving leg includes poles ab on opposite sides of the structure and a sensing leg includes poles cd on an axis essentially perpendicular to that of poles ab, both axes intersecting the symmetrical axis of elongation s of the structure. There may be separation of the axes of poles ab, cd along axis s of elongation, or such axes may, through appropriate pole configuration, be coplanar. In any event, four circumferential flux quadrants $q_1$, $q_2$, $q_3$, $q_4$ are defined as in FIGS. 11 and 12. A structural anomaly affecting any quadrantal flux component will be reflected in output winding WB1. One or more null coils (not shown) may be used for balancing the bridge. An annular field confinement piece may be employed if desired.

Tubular structures other than circular in cross-section may be evaluated magnetically. Device 50 may be modified in shape accordingly, but pole axes of the driving and sensing legs will remain essentially mutually perpendicular and intersect the symmetrical axis of elongation.

In view of the foregoing, it will be seen that several objects of the invention are achieved and other advantages are attained.

Although the foregoing includes a description of the best mode contemplated for carrying out the invention, various modifications are contemplated.

As various modifications could be made in the constructions herein described and illustrated without departing from the scope of the invention, it is intended that all material contained in the foregoing description or shown in the accompanying drawings should be interpreted as illustrative rather than limiting.

What is claimed is:

1. A magnetic bridge for fringing flux evaluation of samples having a substantial degree of conductivity, said bridge comprising a magnetic circuit having at least four arms, a driving leg and a sensing leg, one of said arms being utilized for evaluating at least one sample, the sample-evaluating arm including pole pieces forming end faces for producing a usable core field and defining between them a sample-evaluating gap of the sample-evaluating arm, an electrically conductive gap insert fitted between said pole pieces within said gap, the electrically conductive gap insert extending out and away from the core on all sides of the core except from a selected portion on one side of the core at the sample-evaluating gap for inducing thereby a second field of origin within the gap insert superposed with the core field to produce a stray core field and for providing high reluctance stray flux paths at the gap except in the vicinity of the selected core portion at which there is a low reluctance path for encouraging said stray core field to cross the gap insert and so extend beyond the gap to provide a fringing flux exteriorly of the gap, means for placement of a sample in juxtaposition to the selected core portion at the sample-evaluating gap for causing the sample to be exposed to said fringing flux, whereby the sample changes the fringing flux, driving means associated with the driving leg for providing a time-varying flux path within the four arms of the bridge, and sensing means associated with the sensing leg for sensing changes in the sensing leg caused by changes in the fringing flux resulting from characteristics of the sample.

2. A magnetic bridge according to claim 1 wherein the electrically conductive gap insert is in the gap of more than one arm for producing fringing fluxes for more than one arm.

3. A magnetic bridge according to claim 1 wherein the electrically conductive gap insert at least partially fills the area of the respective gap.

4. A magnetic bridge according to claim 1 wherein at least one gap so partially filled includes at least one shim of electrically conductive and/or magnetic material for balancing of the bridge.

5. A magnetic bridge according to claim 3 wherein the sample extends partially into the area of the partially filled gap.

6. A magnetic bridge device according to claim 1 further comprising means for controlling placement of the sample in juxtaposition to the sample-evaluating gap.

7. A magnetic bridge device according to claim 6 wherein the means for controlling placement of the sample comprises a face plate, the pole pieces of the sample-evaluating arm being positioned relative to the face plate for evaluating samples positioned on a surface of the face plate.

8. A magnetic bridge device according to claim 7 wherein the face plate is electrically conductive, the bridge device further comprising means for providing electrical isolation between the conductive gap insert and at least portions of the face plate which surround the electrically conductive gap insert.

9. A magnetic bridge device according to claim 1 wherein outer end surfaces of the pole pieces which form the sample-evaluating gap establish a first plane and the conductive insert of the sample-evaluating gap has an outer edge surface extending beyond said plane.

10. A magnetic bridge device according to claim 9 wherein the outer edge surfaces of the sample-evaluating gap insert define a second plane skewed at a predetermined angle to the first plane.

11. A magnetic bridge device according to claim 1 wherein the pole pieces and conductive insert together define a nonlinear surface providing conformance with a sample having a nonlinear surface to be evaluated.

12. An accelerometer comprising a movable mass and a magnetic bridge having at least four arms, a driving leg and a sensing leg, one of said arms being mass-position responsive for measuring the position of the mass, the mass-position responsive arm including pole pieces forming end faces for producing a usable core field and defining between them a gap, an electrically conductive gap insert fitted between said pole pieces within said gap, the electrically conductive gap insert extending out and away from the core on all sides of the core except from a selected portion on one side of the core at the gap, for inducing thereby a second field of origin within the gap insert superposed with the core field for providing high reluctance stray flux paths at the gap except in the vicinity of the selected core portion at which there is a low reluctance path for encouraging said core field to cross the gap insert and so extend beyond the gap as a stray core field to provide a fringing flux exteriorly of the gap, means for resiliently supporting of the mass in juxtaposition to the gap for elastic movement of the mass relative to gap in response to accelerations, whereby movement of the mass changes the fringing flux, driving means associated with the driving leg arms for providing a time-varying flux path within the four arms of the bridge, and sensing means associated with the sensing leg for sensing changes in the sensing leg caused by changes in the fringing flux resulting from acceleration-responsive movement of the mass.

13. An accelerometer according to claim 12 wherein the magnetic bridge is formed of H-shaped halves of ferrite material, the conductive gap insert being of electrically conductive material and separating said halves, the bridge thereby defining four gaps, and means for orienting the bridge and mass in relative position for effecting the fringing flux only of the first-said gap by movement of the mass toward and away from the last-said gap.

14. An accelerometer according to claim 13 including an enclosure having opposite ends, the bridge being located proximate one end of the enclosure, the mass being located proximate the other end of the enclosure, and said orienting means presenting a corner of the bridge defining the first-said corner, such that acceleration-responsive movement of the mass is permitted toward and away from the corner on an axis extending between the enclosure opposite ends.

15. An accelerometer according to claim 14 wherein the means for resiliently supporting the mass comprises springs on opposite ends of the mass along said axis.

16. An accelerometer according to claim 15 wherein the means for resiliently supporting the mass comprises an adhesive between the gap and the mass.

17. A magnetic bridge comprising a magnetic circuit having at least four arms, a driving leg and a sensing leg, one of said arms being utilized as an evaluating arm for exposing an object having a substantial degree of conductivity to a fringing flux, whereby changes in the fringing flux caused by the object may be detected and evaluated by use of the magnetic bridge, the evaluating arm including pole pieces forming end faces for producing a usable core field and defining between them an evaluating gap of the evaluating arm, an electrically conductive gap insert fitted between said pole pieces within said gap, the electrically conductive gap insert extending out and away from the core on all sides of the core except from a selected core portion at the evaluating gap, for inducing thereby a second field of origin within the gap insert superposed with the core field and for providing high reluctance stray flux paths at the gap except in the vicinity of the selected core portion for encouraging said core field to cross the gap insert and so extend beyond the gap as a stray core field to provide a fringing flux exteriorly of the gap, means for placement of the object in juxtaposition to the evaluating gap for causing the fringing flux to be affected by the object, driving means associated with the driving leg for providing a time-varying flux path within the four arms of the bridge, and sensing means associated with the sensing leg for sensing changes in the fringing flux resulting from the object.

* * * * *